United States Patent [19]

Harper et al.

[11] Patent Number: 5,714,516
[45] Date of Patent: Feb. 3, 1998

[54] ANTI-VIRAL AGENTS

[75] Inventors: David Richard Harper, Flitwick; Robert Andrew McIlhinney; Caroline Jane Blunt, both of Oxford, all of England

[73] Assignee: British Technology Group Limited, London, England

[21] Appl. No.: 351,307

[22] PCT Filed: May 27, 1993

[86] PCT No.: PCT/GB93/01109

§ 371 Date: Dec. 9, 1994

§ 102(e) Date: Dec. 9, 1994

[87] PCT Pub. No.: WO93/25200

PCT Pub. Date: Dec. 23, 1993

[30] Foreign Application Priority Data

Jun. 10, 1992 [GB] United Kingdom .................. 9212276

[51] Int. Cl.$^6$ .............................. A61K 31/20; A61K 31/10
[52] U.S. Cl. .................................... 514/558; 514/934
[58] Field of Search .............................. 514/558, 934

[56] References Cited

FOREIGN PATENT DOCUMENTS 0 232 982  8/1987  European Pat. Off. .
0 415 902 A1  3/1991  European Pat. Off. .
0 465 423 A2  1/1992  European Pat. Off. .

OTHER PUBLICATIONS

Merck Index 10th Ed 1984 #211 & 212.

Is mail–Cassini et al 113 CA 208251s 1990.

Paige et al (abstract) 1990, FASEP, vol. 4 #7 A 2110.

Paige et al., 1990, Biochemistry, vol. 29, 10566–10573.

McIlhenney, 1990, Trends in Biological Science, vol. 15, pp. 387–391.

*Primary Examiner*—Russell Travers
*Attorney, Agent, or Firm*—Nixon & Vanderhye

[57] ABSTRACT

Compounds of general formula (I)

$$CH_3-(CH_2)_n-\underset{H}{\overset{R}{\underset{|}{\overset{|}{C}}}}-COOH \qquad (I)$$

wherein n is 11, 12 or 13 and R is bromine or hydroxy, and physiologically acceptable salts thereof, with the proviso than when n is 11, R is not bromo, have been found to be effective as non-toxic agents against herpesviruses and retroviruses.

9 Claims, 1 Drawing Sheet

ANTI-VIRAL AGENTS

This is a 371 of PCT/GB93/01109 filed May 27, 1995.

FIELD OF INVENTION

This invention relates to the treatment of diseases caused by herpesviruses, especially by varicella zoster virus.

PRIOR ART

Viruses modify the polypeptides they synthesize in a number of ways. These modifications may result in glycoproteins or lipoproteins which have a wide variety of functions within the virus lifecycle. Lipoproteins are known to play a significant role in infection with many viruses, but their mode of action is poorly understood.

Lipoproteins may arise by the post- or co-translational addition of fatty acids such as palmitic acid and myristic acid. Myristic acid is conjugated to the polypeptide by the enzyme N-myristoyl transferase. Inhibitors of this enzyme have been suggested as being of use as anti-viral agents (R. A. J. McIlhinney, Trends in Biochemical Sciences (1990), 15, 387–391 and L. A. Paige et al., Biochemistry (1990), 29, 10566–10573).

Recently several myristic acid analogue inhibitors of N-myristoyl transferase have been shown to be effective in inhibiting the release of the human immunodeficiency virus (HIV) from HIV infected cells (T. Saermark et al., AIDS (1991), 5, 951–958 and M. L. Bryant et al., Proc. Natn. Acad. Sci. USA (1989), 86, 8655–8659). The analogues shown to be effective are 13-oxamyristic acid and other derivatives wherein a methylene group between $C_4$ and $C_{13}$ is substituted by an oxygen or sulphur atom. Although effective, the best of these derivatives has been shown to be toxic to the infected cells. In all cases described the infective virus has been a retrovirus such as HIV or *Rashid sarcomavirus* (RSV). A non-toxic inhibitor of myristoylation would therefore be of value. The activity in HIV is in no way indicative of activity in other viruses. Viruses are categorised into a wide range of groups and retroviruses, such as HIV, have a unique replication strategy. HIV is a particularly diverse virus especially in that it is an RNA virus. Thus, few generalities can be brought from data originating from HIV experiments.

SUMMARY OF THE INVENTION

It has now been found that certain other derivatives of myristic acid are effective in inhibiting herpesviruses with minimal cytotoxic effect on the infected cells. These derivatives are also of use in inhibiting retroviruses such as HIV when dissolved in an appropriate solvent. This is the first non-retroviral effect of any myristic acid analogue to be demonstrated.

Accordingly the invention provides the use of a compound of general formula (I)

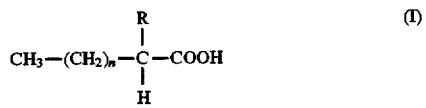

(I)

wherein n is 11, 12 or 13 and R is bromine or hydroxy, and physiologically acceptable salts thereof, for the manufacture of a medicament for use in the treatment of herpesvirus infections, with the proviso than when n is 11, R is not bromo.

The term "herpesvirus infections" includes any infection or disease caused by a virus classified as a herpesvirus, especially herpes simplex virus (HSV), varicella zoster virus (VZV), cytomegalovirus (CMV) and Epstein-Barr virus (EBV).

The compounds of general formula (I) when dissolved in a suitable solvent are also of use for the manufacture of a medicament for use in the treatment of retroviral infections, for example HIV.

Although the prior art discloses the use of 13-oxamyristic acid and other related derivatives of myristic acid, the compounds of use in the present invention differ in preserving the natural alkyl chain backbone of the fatty acid and placing substituents on that backbone chain. This results in compounds that are effective and non-toxic against non-retroviruses as well as retroviruses.

BRIEF DESCRIPTION OF THE ACCOMPANYING DRAWING

FIG. 1 shows the effect of 2-hydroxymyristic acid on VZV (line with boxes) and HSV (line with triangles) over a range of concentrations.

DESCRIPTION OF THE PREFERRED EMBODIMENTS

Figure 1:
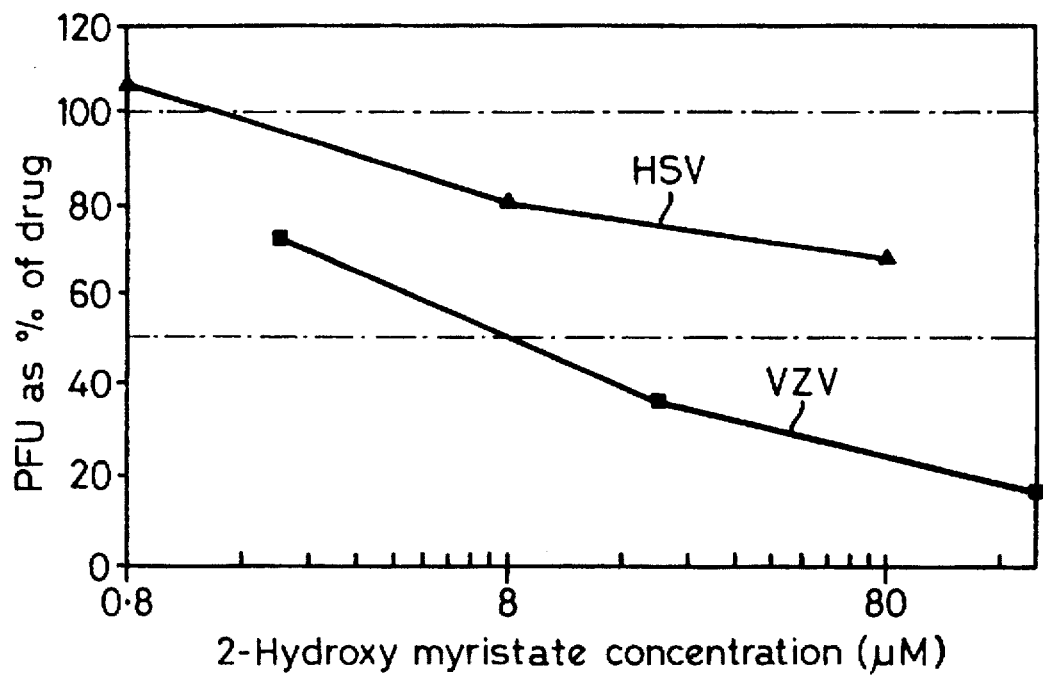

The preferred compounds of use in the present invention are 2-bromopalmitic acid, 2-hydroxymyristic acid and 2-hydroxypalmitic acid, especially 2-hydroxymyristic acid and 2-hydroxypalmitic acid. All these compounds may exist as stereoisomeric enantiomers. It is preferable that the compound of use is the (—) or laevrorotatory isomer. These compounds are effective against herpesviruses, especially varicella zoster virus (VZV) when dissolved in a variety of commonly used pharmaceutical solvents. They are also of use against retroviruses such as HIV, but in both cases show a preference for non-dimethylsulphoxide-like solvents. A suitable solvent for their use against HIV would be ethanol and similar solvents.

The activity against non-retroviruses is also improved by the presence of a non-dimethylsulphoxide-like solvent such as ethanol.

The compounds of formula (I) in the present invention are available from recognised chemical suppliers, e.g. Aldrich, Sigma. The compounds may be used in their free form or when as a salt, particularly as a salt with a base, suitable bases are the alkali metal hydroxides, for example, sodium hydroxide, quaternary ammonium hydroxides and amines such as tris (tris representing 2-amino-2-hydroxymethyl propane 1,3-diol).

The use of the invention may be described as a method of treating a patient suffering from a herpesvirus or retroviral infection, which comprises administering to the patient a therapeutically effective dosage of the compounds of general formula (I) or a physiologically acceptable salt thereof.

The compound is administered in any pharmaceutically acceptable form but preferably takes the form of a topical formulation.

A range of dosage for the compounds of general formula (I) in the above treatment is similar to the dosages of Acyclovir (Wellcome UK) used in the treatment of those infections as set out in the ABPI Data Sheet Compendium 1991–1992.

The compounds of general formula (I) may be formulated with a physiologically acceptable diluent or carrier for use as pharmaceuticals particularly for human use by a variety of methods. For instance, it may be applied as a composition incorporating a liquid diluent or carrier, for example an aqueous or oily solution, suspension or emulsion, which may often be employed in injectable form for parenteral administration and therefore may conveniently be sterile and pyrogen free. Oral administration may also be used, although compositions for this purpose may incorporate a liquid diluent or carrier, it is more usual to use a solid, for example a conventional solid carrier material such as starch, lactose, dextrin or magnesium stearate. Such solid compositions may conveniently be of a formed type, for example as tablets, capsules (including spansules), etc.

Other forms of administration than by injection or through the oral route may also be considered in both human and veterinary contexts, for example the use of suppositories or pessaries. Another form of pharmaceutical composition is one for buccal or nasal administration, for example lozenges, nose drops or an aerosol spray, or alternatively drops for administration into the eye which may conveniently contain a sterile liquid diluent or carrier.

It may be desired that the compound is administered topically in the form of creams, lotions or drops including shampoos.

EXAMPLES

Example 1

Effect of 2-hydroxymyristic acid on *Varicella zoster* virus (VZV)

2-Hydroxymyristic acid, 13-oxamyristic acid and N-myristoyl glycinol diethylacetal (GoA) were assayed for activity against VZV.

The assay system used was the Mewo cell plaque reduction assay of VZV, C. Grose and P. A. Brunell, Infection & Immunity, 19, 199–203 (1978). (The Mewo cell line is available from C. Grose, University of Iowa, Iowa, USA.) VZV does not form clearly defined plaques in MRC5 cells, and for this reason the Mewo cell line was used to allow plaque assay. Compounds were tested at levels from 2 to 200 μM. After staining, it was apparent that 13-oxamyristic acid was toxic to cells at 200 μM, while GoA did not cause 50% inhibition of virus at any concentration tested. In contrast, 2-hydroxymyristic acid showed inhibition at 20 and 200 μM, with an apparent 50% inhibitory concentration ($IC_{50}$) of 8 μM. FIG. 1 shows the effect of 2-hydroxymyristic acid on VZV (line joined by boxes). The concentration of 2-hydroxymyristic acid is shown on the abscissa and the reduction in plaque forming unit (PFU) as compared to the control having no test compound present. At the highest concentration of 2-hydroxymyristic acid, crystalline deposits were observed. The $IC_{50}$ of 8 μM is comparable with the range of 1.6–5.1 μM reported for acyclovir in VZV assay[12].

In order to characterise the nature of the antiviral effect, the effect of 2-hydroxymyristic acid on the synthesis of viral antigen was assayed by immunoblotting. With an inoculum of one infected cell to four uninfected cells, harvested at three days post-infection (70–80% cytopathic effect), no reduction in antigen synthesis was apparent even with 2-hydroxymyristate present at 80 μM ($10\times IC_{50}$). However, when the initial inoculum was reduced, and the time of harvest correspondingly increased, inhibition was apparent, and this was inversely proportional to the inoculum used. VZV spreads in MRC5 monolayers by the formation of syncytia, and these results strongly suggest that the effect of 2-hydroxymyristate was to inhibit syncytium formation rather than viral protein synthesis in the initially infected cell.

Cytotoxicity was assessed by the incorporation of radiolabelled precursors to assay protein synthesis and myristoylation in the infected cell. A high (1:4) inoculum was used so as to prevent any overall decrease in virus infection of the MRC5 monolayer, and 2-hydroxymyristic acid was again assayed from 0.1 to $10\times IC_{50}$. It was clear that total protein synthesis (measured by incorporation of $^{35}S$ methionine) was unaffected at any concentration tested, further suggesting that 2-hydroxymyristic acid was not toxic to cells.

From the above data, it is clear that 2-hydroxymyristic acid is producing a non-specific inhibition of myristoylation, and that this is resulting in a specific antiviral effect without producing significant cellular toxicity even at levels ten times greater than the $IC_{50}$.

Example 2

Effect of 2-hydroxymyristic acid on herpes simplex virus (HSV)

The Vero cell plaque assay was performed on HSV as described in C. S. Crumpacker et al., N. Eng. J. Med (1982), 306, 343–346, and using 2-hydroxymyristic acid over the range 0.8 μM to 80 μM. FIG. 1 shows the effect of 2-hydroxymyristic acid on HSV (line joined by triangles).

Example 3

The VZV plaque assay of Example 1 was repeated using a variety of myristic acid analogues. Briefly, sub-confluent Mewo monolayers (Grose and Brunell, 1978, supra) in 24 well plates were infected with approximately 40 P.F.U. (Plaque Forming Units) of cell-free varicella zoster virus (VZV) strain H-551. After an adsorption period of 2 hours the cells were overlaid with 750 μl of MEM (Minimum Essential Medium (Eagle)) supplemented with 2% fetal calf serum and 1% non-essential amino acids. The anti-viral compounds to be tested were solubilized in ethanol, added to final concentrations of 0, 2, 20 or 200 μM and the wells then overlaid with a further 750 μl of MEM supplemented with 2% fetal calf serum, 1% non-essential amino acids and 0.3% agarose. Mock infected wells were also included as controls to test for cytotoxicity. All plates were incubated at 32° C. with 5% $CO_2$. Eight days post infection the monolayers were fixed in 4% formaldehyde and stained with crystal violet. Plaques were counted and the $IC_{50}$ values (the concentration causing a 50% reduction in plaque numbers) were calculated by interpolation. The $IC_{50}$ values and an index of cytotoxicity is presented in Table 1 below.

TABLE 1

| Test Compound | $IC_{50}$ Against VZV (μM) | Toxicity in Mewo Cells |
|---|---|---|
| a) 2-azidotetradecanoic acid | $IC_{50}$ unobtainable | ++++ |
| b) 2-bromotetradecanoic acid | 14.75 | +++ |
| c) 9-(butylamino)nonanoic acid | 164.2 | − |
| d) 11-(ethylamino)undecanoic acid | $IC_{50}$ unobtainable | − |
| e) 2-(ethyloxy)undecanoic acid | 14.4 | ++ |
| f) glycidic acid | 4.5 | +++ |
| g) 2-hydroxypalmitic acid | 14.2 | − |
| h) myristoylmethylamide | 56.6 | + |
| i) 2-hydroxytetradecanoic acid | 21.5 | − |
| j) 2-hydroxytetradecanoic acid (−) | 11.5 | − |
| k) 2-hydroxytetradecanoic acid (+) | 48.7 | − |
| l) 11-(ethylthio)undecanoic acid | $IC_{50}$ unobtainable | +++ |
| m) 12-(methyloxy)dodecanoic acid | 17.3 | +++ |

TABLE 1-continued

| Test Compound | IC$_{50}$ Against VZV (μM) | Toxicity in Mewo Cells |
|---|---|---|
| n) N-myristoylglycinaldiethylacetal (GoA) | IC$_{50}$ unobtainable | — |
| o) 2-bromopalmitic acid | 0.89 | +++ |

Key
− no apparent cytotoxicity
+ thinning of monolayer at high concentration
++ pronounced thinning of monolayer at high concentration
+++ destruction of monolayer at 200 μM concentration
++++ destruction of monolayer at 20 μM concentration The most effective myristic acid derivatives in the assay that failed to be cytotoxic were 2-hydroxymyristic acid racemic mixture and the isomers thereof, i), j) and k). 2-Bromopalmitic acid, although toxic at 200 μM is included in the present invention as the difference between is IC$_{50}$ and its toxic level is sufficient that it is unlikely to be toxic at a therapeutic level. It therefore possesses the advantages of the claimed invention.

The discrepancy in the IC$_{50}$ values of 2-hydroxymyristic acid in Examples 1 and 3 points towards a range of IC$_{50}$ from 8 μM at the lower end to 33 μM at the upper end. Both these figures are comparable to the performance of acyclovir in the described VZV assay (Boyd M. R. et al., Antimicrob. Agents & Chemotherapy (1987), 31, 1238–1242.

Example 4

The effect of 2-hydroxymyristic acid (2-HM) on VZV or HIV when solubilized in a variety of solvents was observed using the methods approved for the Medical Research Council AIDS Directed Programme as described in H. C. Holmes et al., Antiviral Chem. & Chemother. (1991), 2(5), 287–293, using concentrations of 2 HM from 0.08 to 1000 μM. Additionally, back titration assays of HIV were carried out by adding supernatants from treated infected cells to uninfected C8166 cells at increasing dilutions. Assays were scored by recording the presence or absence of syncytium formation.

Preparation and assay of VZV was carried out as described previously in Examples 1 and 3.

The HIV assays were performed at three of the MRC approved laboratories (Mill Hill, Cambridge and St. Bartholomew's Hospital).

Stocks of 2-HM were prepared from crystalline solid by dissolving in ethanol or in dimethyl sulphoxide (DMSO) to a concentration of 20 mM to 100 mM, and were stored at −20° C. prior to addition to culture media. Concentrations of 2-HM greater than 80 to 100 μM are imprecise, since 2-HM crystallises from aqueous solutions at such levels.

As shown in Table 2 below, 2-HM inhibits the replication of both VZV (St. Bartholomew's Hospital) and HIV (Mill Hill) when solubilised in ethanol. However, when the results from the different test centres for HIV were compared, it was clear that solubilisation of 2-HM in DMSO (as initially used at St. Bartholomew's Hospital) resulted in a lack of any significant anti-viral effect despite apparent solubility of 2-HM in this solvent. In the light of the results obtained for VZV, 2-HM was re-tested against HIV at St. Bartholomew's Hospital using ethanol as the solvent. In this assay, a clear anti-viral effect was apparent, although at levels somewhat higher than those observed at Mill Hill. In both the St. Bartholomew's Hospital and the Mill Hill assay, toxicity of 2-HM to C8166 cells was detected, but only at levels above those at which 2-HM would crystallise from aqueous solution.

Experiments comparing the anti-viral activity of 2-HM against VZV using ethanol and DMSO solvents showed a similar effect, with no significant anti-viral effect produced by 2-HM solubilised in DMSO.

TABLE 2

| Anti-viral efects of 2-hydroxymyristic acid | | | | |
|---|---|---|---|---|
| | | Ethanol | | DMSO | |
| Virus | Assay | IC$_{50}$ | TC$_{50}$ | IC$_{50}$ | TC$_{50}$ |
| VZV | Plaque reduction[1] | 33.1 | >200 | >200 | >200 |
| HIV | Antigen assay[1] | 31.4 | 168 | 220 | >400 |
| | Antigen assay[2] | 2.0 | 192 | ND | ND |
| | Virus titration[2] | 3.9 | 192 | ND | ND |

[1]Medical College of St. Bartholomew's Hospital, London.
[2]Medical Research Council Collaborative Centre, Mill Hill.

This example shows the importance that should be attached to the choice of solvent for anti-viral agents. The improved IC$_{50}$ value observed for 2-HM in ethanol was surprising and shows that this compound and similar ones, when solubilised in the appropriate solvent, are effective against HIV.

We claim:

1. A method of treating herpesvirus infections in a patient in need of such treatment, said method comprising the step of administering to a patient in need of such treatment a compound of formula (I)

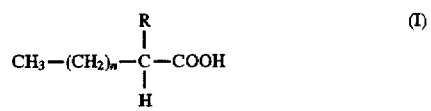

wherein n is 11, 12 or 13 and R is bromine or hydroxy, and physiologically acceptable salts thereof with the proviso that when n is 11, R is not bromo.

2. The method according to claim 1, wherein R is hydroxy.

3. The method according to claim 2, wherein n is 11.

4. The method according to claim 2, wherein n is 13.

5. The method according to claim 2, wherein the compound is (−)2- hydroxymyristic acid.

6. The method according to claim 1, wherein the herpesvirus is varicella zoster virus.

7. The method according to claim 1, wherein the compound of formula (I) is solubilised in a non-dimethylsulphoxide-like solvent.

8. The method according to claim 1, wherein the compound is 2- palmitic acid.

9. The method according to claim 1, wherein the compound the compound of formula (I) is 2-bromopalmitic acid.

* * * * *